United States Patent [19]

Dubreuil

[11] Patent Number: 5,336,389
[45] Date of Patent: Aug. 9, 1994

[54] LONG LASTING ALKALI AND ALKALINE EARTH METAL SENSOR

[75] Inventor: Alain Dubreuil, Hull, Canada

[73] Assignee: Her Majesty the Queen in right of Canada, as represented by the Minister of Energy, Mines and Resources, Ottawa, Canada

[21] Appl. No.: 895,044

[22] Filed: Jun. 8, 1992

[51] Int. Cl.$^5$ .......................................... G01N 27/411
[52] U.S. Cl. ................................ 204/422; 204/153.15
[58] Field of Search .................... 204/153.15, 153.18, 204/421–429

[56] References Cited

U.S. PATENT DOCUMENTS

| | | | |
|---|---|---|---|
| 3,794,569 | 2/1974 | Kawai et al. | 204/422 |
| 4,166,019 | 8/1979 | Roy et al. | 204/422 |
| 4,217,179 | 8/1980 | Fray | 204/422 |
| 4,645,571 | 2/1987 | Dubreuil et al. | 204/422 |
| 5,112,456 | 5/1992 | Worrell et al. | 204/422 |

FOREIGN PATENT DOCUMENTS 1470558 4/1977 United Kingdom.
1602564 11/1981 United Kingdom.

*Primary Examiner*—T. Tung
*Attorney, Agent, or Firm*—Jacobson, Price, Holman & Stern

[57] ABSTRACT

A method and device is disclosed permitting accurate, reproducible assay of alkali metal and alkaline earth metal contents of molten aluminum over an extended period of use. The sensor of the present invention uses as a reference electrode a calibrated quantity of a sodium-gallium or sodium-indium alloy in the form of a two-phase intermetallic reference system.

9 Claims, 4 Drawing Sheets

LONG LASTING ALKALI AND ALKALINE EARTH METAL SENSOR

BACKGROUND OF THE INVENTION

This invention relates to a long lasting sensor for determining the alkali and alkaline earth metal contents of molten aluminum.

During the refining of aluminum, it is necessary to reduce the sodium and lithium contents of molten aluminum to the order of a few parts per million, particularly if thin sheets are to be rolled or wire is to be extruded from the refined product.

In some Al-Si alloys, Na or Sr is added in concentrations of the order of magnitude of hundreds of ppm as a structural modifier to improve the physical properties. Since Na and Sr are very reactive metals, the efficiency of the addition is variable.

Similarly, the lithium concentration of some Al-Li alloys is in the order of several weight percent.

To produce good quality alloys, the ability to perform accurate analysis of the sodium, lithium and strontium is required.

DESCRIPTION OF THE PRIOR ART

Hitherto, during the refining of aluminium, the sodium, lithium and strontium contents of the molten aluminum have been monitored by spectroscopic analysis of solidified samples of the molten alloy. However, such technique requires samples of molten metal to be taken, cast, prepared and analyzed in the laboratory by spectroscopy, which is both time-consuming and laborious. This prior procedure is thus a batch process.

In British Patent No. 1,470,558 (Fray) an electrochemical sensor based on $\beta$-alumina is described, for measuring the sodium concentration in molten aluminum. The reference material used by Fray is solid and comprises a mixture of $\alpha$-alumina and $\beta$-alumina in equilibrium with oxygen from atmospheric air. However, the experimental results obtained do not agree with Nernst's Law, since the sodium concentration varies in a linear manner with the emf generated between the electrodes. As a result, such a sensor lacks precision and reproducibility.

In British Patent No. 1,602,564 (Fray), an improved version of the above sensor is proposed, consisting of an airtight sensor in which the reference material comprises a mixture of $\alpha$-alumina, $\beta$-alumina and a mixture of a metal and a metal oxide such as $Cu/Cu_2O$, $Cr/Cr_2O_3$ or $Ni/NiO$. The experimental results obtained still do not have a reproducibility sufficient to enable such sensor to be useful in the metallurgical industry.

U.S. Pat. No. 4,645,571 (Dubreuil et al) describes an electrochemical sensor based on $\beta$-alumina for measuring mainly the sodium and lithium contents in molten aluminum. The reference material mixture fixes the activity of sodium or lithium at the operating temperature. The reference material mixture is a slurry of salts and molten metallic aluminum. Precise and reproducible results could generally be obtained. However, such a sensor needs at least 30 minutes of conditioning at the operating temperature to obtain a meaningful electrochemical potential. Moreover, due to the preferential evaporation of some components of the reference material, the life of the sensor was limited to 8 hours. Such sensors are not reusable since remelting of the reference material would crack the $\beta$-alumina tube.

SUMMARY OF THE INVENTION

An object of the present invention is to provide a method and device permitting accurate, reproducible assay of alkali metal and alkaline earth metal contents of molten aluminum over an extended period of use.

Another object is to provide a device which affords a continuous, on-line, long-term readout of the sodium, lithium and/or strontium contents in an aluminum melt.

Accordingly, the invention provides a sensor for determining the alkali and/or alkaline earth metal content of molten aluminum, which forms a working electrode at one end of a solid electrolyte rod, made of either $\beta$- or $\beta''$- alumina and which is adapted to be immersed in the molten aluminum, a reference electrode in contact with the other, cooler end of the solid electrolyte rod, said reference electrode being formed by a calibrated quantity of an alloy of sodium-gallium or sodium-indium alloy, wherein said alloy forms a two-phase intermetallic reference system, an electronic conductor to close the circuit through the intermediary of the molten aluminum, and means for determining the emf generated between the electrodes.

The present invention also provides a method for determining the alkali and/or alkaline earth metal content of molten aluminum which forms a working electrode at one end of a solid electrolyte rod made of either $\beta$- or $\beta''$-alumina, the reference electrode at the other end being formed by a calibrated quantity of sodium-gallium or sodium-indium alloy, wherein said alloy is a two-phase intermetallic mixture, and an electronic conductor to close the circuit through the intermediary of the molten aluminum, and means for determining the emf generated between the electrodes.

Thus, the invention affords a potentiometric sensor in the form of a galvanic cell for measuring, over the long term, the concentrations of sodium, lithium and strontium in molten aluminum.

The sensitivity and precision of a potentiometric sensor will normally be sufficient for industrial applications as long as potential at the reference electrode does not drift.

As the solid electrolyte, the sensor of the invention preferably uses $\beta$-alumina or $\beta''$-alumina which are two solids with very high ionic conductivities, the mechanism of conduction being the movement of $Na^+$ through their crystal lattices. For sensor applications, $\beta$-alumina is very selective to sodium and lithium; $\beta''$-alumina is selective to alkali metals (lithium, sodium, etc.) and to alkaline-earth metals (magnesium, calcium, strontium).

Conventionally, most galvanic cells are designed to function at one temperature. However, in the present invention, the reference electrode is maintained at a much lower temperature than the working electrode, thereby ensuring a long-term stability of the sensor. This concept is developed subsequently herein with different examples.

Thus, the invention uses a two-phase metallic system to fix the activity of a component, in which the reference electrode operates at a much lower temperature than the working electrode. As a result, the operating life of the sensor is very long and it can, furthermore, be incorporated in the lining of the furnace.

If $\beta$-alumina is used as a solid electrolyte separating two electrode compartments in a galvanic cell at a constant temperature T1 and the activity of sodium in the reference is $(a_{Na})$ref and the activity of sodium in the molten aluminum is $(a_{Na})$working:

$$\begin{array}{cc} a_{Na}|\beta\text{-alumina}| & a_{Na} \\ \text{ref} & \text{working} \\ T_1 & T_1 \end{array} \qquad (1)$$

wherein $T_1$ is the temperature in Kelvin, R is the gas constant and F is Faraday's constant. Then the cell potential E is given by the following equation:

$$E = -RT_1/F \ln (a_{Na})\text{ref} + RT_1/F \ln (a_{Na})\text{working} \qquad [1]$$

If sodium and lithium are present at the working electrode:

$$\begin{array}{cc} a_{Na}|\beta\text{-alumina}| & a_{Na}, a_{Li} \\ \text{ref} & \text{working} \\ T_1 & T_1 \end{array} \qquad (2)$$

then the cell potential is given by:

$$E = E° + RT_1/F \ln (a_{Na} + k\beta Li\ a_{Li}) \qquad [3]$$

where $k\beta Li$ is a function of the element (Li, Sr . . . ) and of the type of ceramic used ($\beta$ or $\beta''$-alumina).

In another example, A. A. Dubreuil, A. D. Pelton, D. Doutre and G. Dube, "Solid Electrolyte Probes to Monitor the Alkali and Alkaline Earth Content of Molten Aluminum.", Light Metals 1988, ed. L. G. Boxall (Phoenix, Ariz.: Metallurgical Society of AIME (1988) 495–499, showed that a potentiometric sensor for alkaline-earth metal can be made with $\beta''$-alumina as a solid electrolyte and a reference mixture (containing Al, Na$_3$AlF$_6$, NaF and NaCl) which fixes the activity of sodium.

The galvanic cell can be represented as:

$$\begin{array}{cc} a_{Na}|\beta''\text{-alumina}| & a_{Sr} \\ \text{ref} & \text{working} \\ T_1 & T_1 \end{array} \qquad (3)$$

then the cell potential is given by:

$$E = E° + RT_1/2F \ln (k\beta''Sr\ a_{Sr}) \qquad [4]$$

Because Sr is divalent, coefficient 2 is present in the denominator.

For $\beta$-alumina, $k\beta Mg$, $k\beta Ca$ and $k\beta Sr$ are null.

A non-isothermal cell can be represented as:

$$\begin{array}{cc} a_{Na}|\beta\text{-alumina}| & a_{Na} \\ T_0 & T_1 \end{array} \qquad (4)$$

and if the activity of sodium is the same on each side of the solid electrolyte, the emf is given by:

$$E = S(T_1 - T_0) \qquad [5]$$

where S, known as the Seebeck coefficient, is a function of the ceramic.

For the present case with sodium and lithium present and a non-isothermal reference, the resultant cell, in effect, amounts to the summation of cells (2) and (4):

$$\begin{array}{ccc} a_{Na}|\beta\text{-alumina}| & a_{Na}, a_{Li} \\ \text{ref} & & \text{working} \\ T_0 & & T_1 \end{array} \qquad (5)$$

where the emf is given by:

$$E = E° + S(T_1 - T_0) + RT_1/F \ln(a_{Na} + k\beta Li\ a_{Li}) \qquad [6]$$

where $E°$ is a function of $T_0$.

Similarly, the emf for a non-isothermal sensor is related to the activity of strontium by:

$$E = E° + S''(T_1 - T_0) + RT_1/2F \ln (k\beta''Sr\ a_{Sr}) \qquad [7]$$

A practical potentiometric sensor requires a suitable reference electrode. The criteria for the selection of a reference system are:

The activity of sodium must be fixed at the reference electrode.

The reference electrode should be reversible. Ideally the concentration of sodium is important.

The operating temperature span is at least 100° C. and within the overall range of 60° to 300° C.

A knowledge of the exact composition of the reference is not required.

The vapour pressure of the enclosed reference system is low to minimise stress.

Applicants have selected two systems to provide the reference electrode; these systems being based on Na-Ga and Na-In. Both gallium and indium have low melting points and form intermetallic compounds with sodium.

BRIEF DESCRIPTION OF THE DRAWINGS

Embodiments of the invention will now be described, by way of example, with reference to the accompanying drawings, in which.

DESCRIPTION OF THE PREFERRED EMBODIMENTS

Figure 1A:
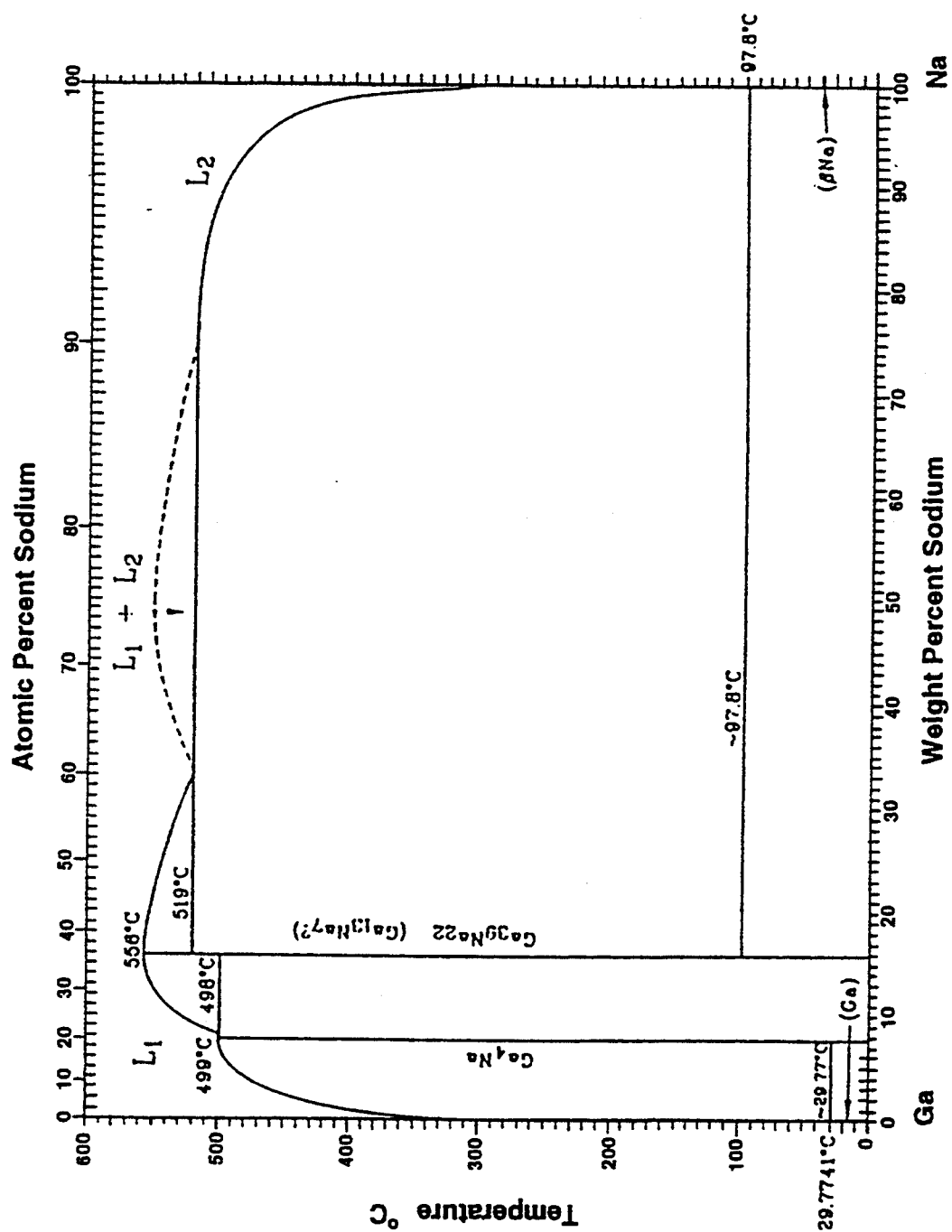
FIGS. 1A and 1B show graphically the phase diagrams for gallium and sodium.
Figure 1B:
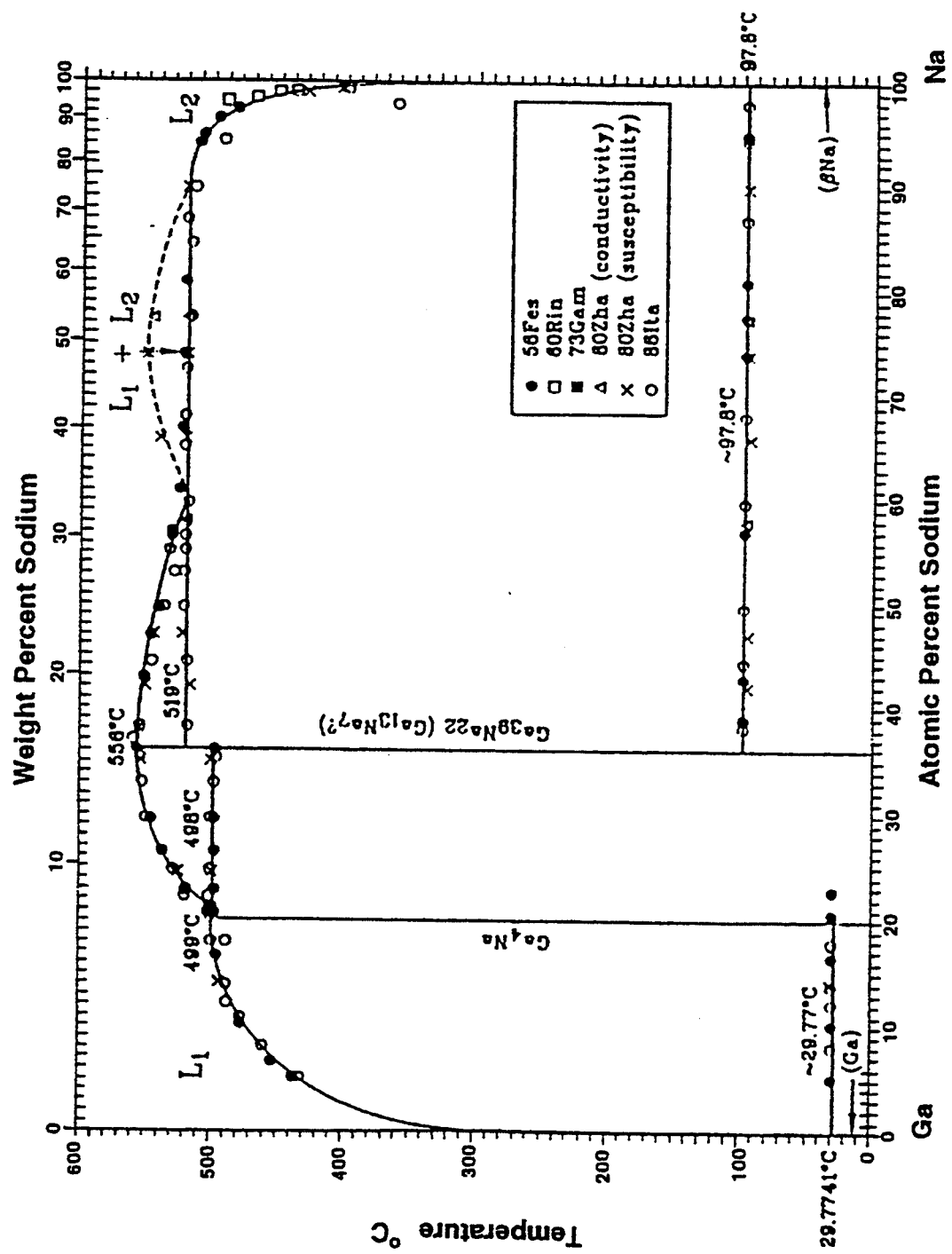

Referring now to FIG. 1, the Ga-Na system has been reviewed critically recently by A. D. Pelton and S. Larose, "The Ga-Na (Gallium-Sodium) System":, Bull. of Alloy Phase Diagrams, Vol. 11 No. 4 (1990) 347–353. Ga has a melting point of 29.7° C. On the Ga rich side of the phase diagram, the first compound is Ga$_4$Na with a melting point of 499° C. Below 300° C., Ga$_4$Na is sparingly soluble in molten Ga. For a given temperature, the activity of sodium is constant at a given temperature in the two-phase region (Ga(l) and Ga$_4$Na(s)). It is not necessary to know the exact composition of the system as long as operation takes place in the two-phase region.

The vapour pressures of sodium and gallium, over that composition range, as a function of the temperature, can be calculated from the data of Pelton and Larose. At 100° C., $P_{Na} = 10^{-10}$ atm, $P_{Ga} = 10^{-32}$ atm and at 300° C., $P_{Na} = 2 \times 10^{-5}$ atm, $P_{Ga} = 10^{-19}$ atm. There will be no pressure build-up during the operation.

Figure 2:
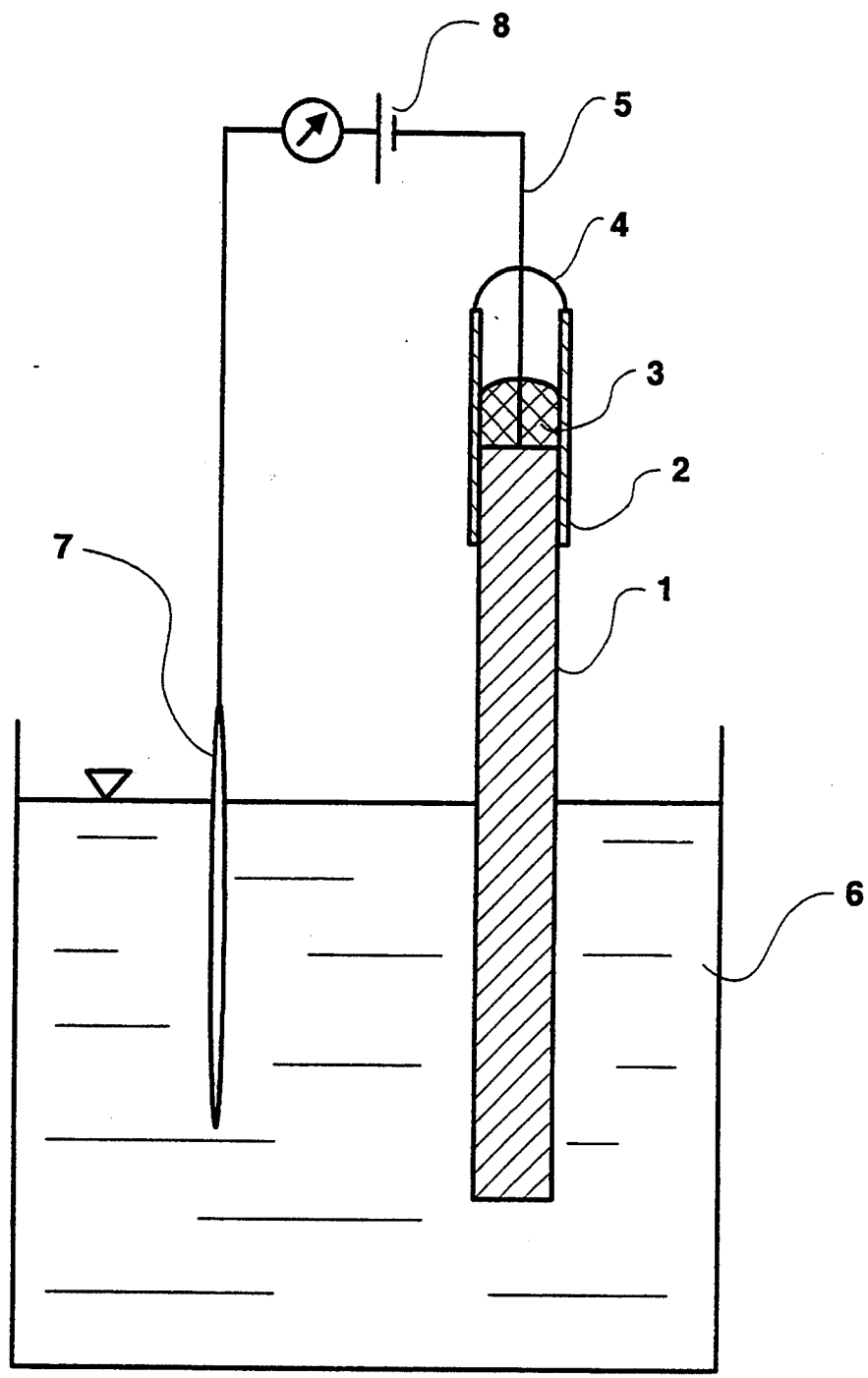
FIG. 2 is a diagrammatic sectional view of a sensor.

Referring now to FIG. 2, the system comprises a solid rod 1 of $\beta$- or $\beta''$-alumina (depending of the use of the sensor) brazed to a metallic tube 2 (formed of KOVAR). A weighed quantity 3 of gallium is introduced into the tube 2 and a glass seal 4 encloses the system. A tungsten wire 5 passes through the glass seal 4 and contacts the gallium.

To prepare the reference electrode and referring still to FIG. 2, the other end of the rod 1 is brought into contact with a molten salt 6 containing sodium ions, such as NaCl or NaCl-NaNO$_3$. An electronic conductor 7, typically formed of platinum, contacts the melt. Then passage of a known quantity of current from a generator 8, ensures a control addition of sodium to the gallium.

Figure 3:
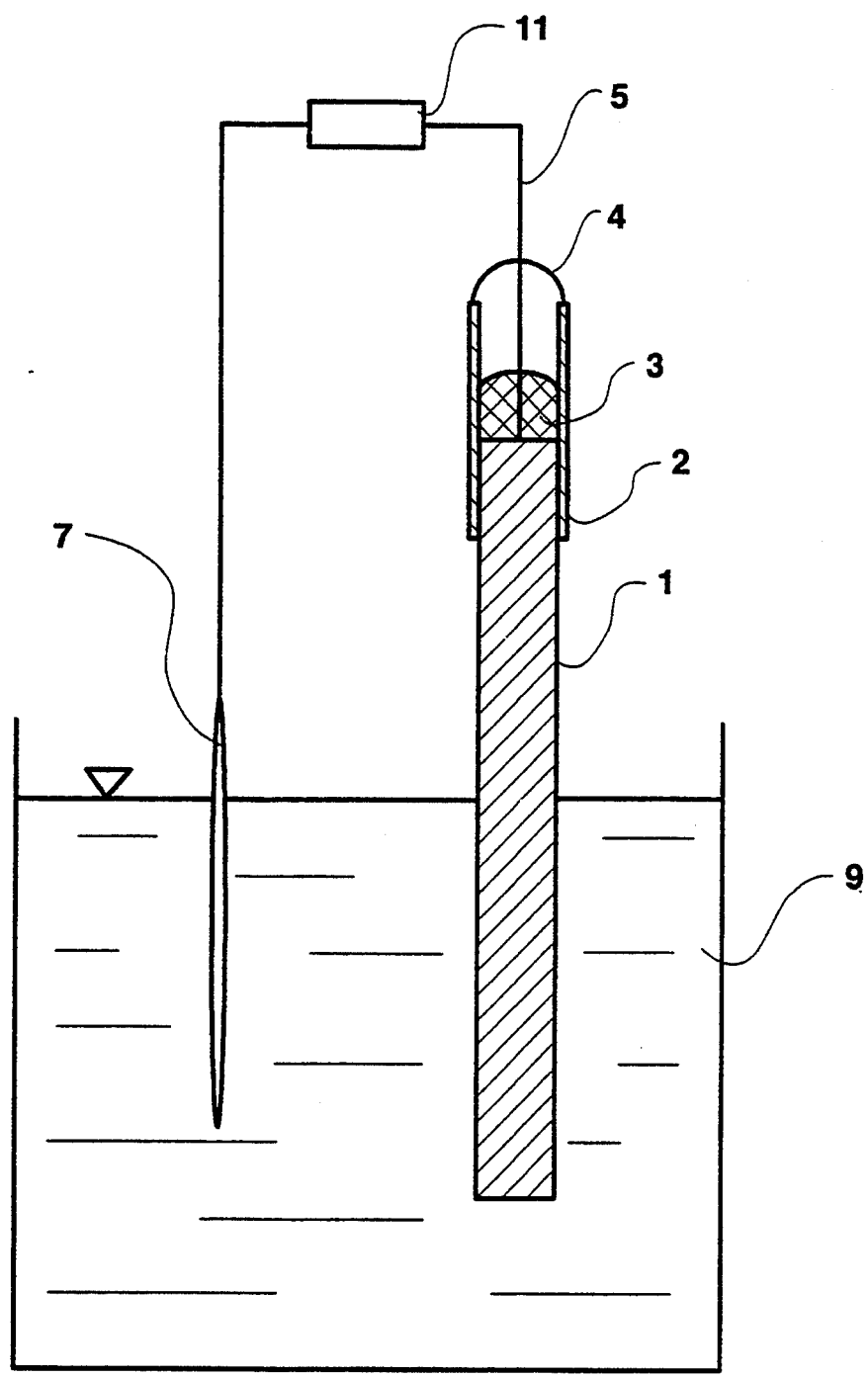
FIG. 3 is a diagrammatic sectional view of a potentiometric sensor.

With the potentiometric sensor now ready for industrial use and referring to FIG. 3, the $\beta$ alumina or $\beta''$ rod 1 and the platinum conductor 8 of the sensor are contacted with molten aluminum 9. The emf (voltage) generated between the electronic conductor 7 and the tungsten wire 5 is measured by a high impedance input data acquisition system 11. The temperature of the reference and the temperature of the aluminum may then also be measured.

We claim:

1. A sensor for determining the alkali and/or alkaline earth metal content of molten aluminum comprising: a molten aluminum working electrode at one end of a solid electrolyte rod, made of either $\beta$- or $\beta''$-alumina; a reference electrode in contact with the other end of the solid electrolyte rod, the reference electrode being formed by a calibrated quantity of sodium-gallium or sodium-indium alloy; means for connecting the working electrode and the reference electrode and means for determining the emf generated therebetween; said sensor being arranged such that, during operation of the sensor, the sodium-gallium or sodium-indium alloy of the reference electrode is maintained as a mixture of a liquid phase of gallium or indium and a solid phase of an intermetallic compound of sodium and gallium or sodium and indium.

2. A sensor according to claim 1, wherein the sensor is capable of operating in a non-isothermal mode such that the reference electrode functions at a significantly lower temperature then the working electrode.

3. A sensor according to claim 2, wherein the reference electrode operates within a temperature range of from about 60° to 300° C.

4. A sensor according to claim 3, wherein the reference electrode fixes the activity of sodium at a given temperature within the operating temperature range of the reference electrode.

5. A sensor according to claim 1, adapted for incorporation in the lining of a furnace.

6. A sensor according to claim 1, wherein the alkaline earth metal to be determined is magnesium, calcium or strontium.

7. A sensor according to claim 1, wherein the alkaline earth metal to be determined is magnesium, calcium or strontium and the solid electrolyte is $\beta''$-alumina.

8. A sensor according to claim 1, wherein the alkali metal to be determined is lithium or sodium.

9. A sensor according to claim 1, wherein the alkali metal to be determined is lithium or sodium and the solid electrolyte is $\beta$-alumina.

* * * * *